United States Patent
Flashinski et al.

(10) Patent No.: US 6,551,560 B1
(45) Date of Patent: Apr. 22, 2003

(54) TWO-STAGE DISPENSING MAT

(75) Inventors: Stanley J. Flashinski, Racine, WI (US); Daniel T. Ropiak, Kenosha, WI (US); Donald W. Hildebrandt, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 195 days.

(21) Appl. No.: 09/652,561

(22) Filed: Aug. 31, 2000

(51) Int. Cl.[7] .......................... A62B 7/08; A01G 13/06; A24F 25/00; B01D 47/00; A21B 1/00

(52) U.S. Cl. ................... 422/125; 422/261; 422/285; 422/305; 422/306; 392/386; 392/390; 392/391; 392/392; 392/393; 239/34; 239/57; 239/60; 239/136; 261/26; 261/101; 261/104; 261/DIG. 88; 261/DIG. 89; 219/392; 219/435; 219/524; 219/541

(58) Field of Search .................. 422/1, 5, 28–29, 422/32–37, 122–125, 164, 190, 211, 244, 261, 285, 292, 305–307; 392/390, 386, 393, 392, 391; 239/136, 34, 60, 57; 261/26, 101, 104, DIG. 88, DIG. 89; 219/392, 541, 524, 435

(56) References Cited

U.S. PATENT DOCUMENTS

| | | | |
|---|---|---|---|
| 2,154,803 A | * | 4/1939 | Bancroft |
| 3,620,453 A | | 11/1971 | Gancberg et al. ............ 239/60 |
| 4,037,352 A | * | 7/1977 | Hennart et al. ............... 43/129 |
| 4,037,353 A | * | 7/1977 | Hennart et al. |
| 4,214,146 A | * | 7/1980 | Schimanski |
| 4,439,415 A | * | 3/1984 | Hennart et al. |
| 5,139,864 A | | 8/1992 | Lindauer ................. 428/304.4 |
| 5,657,574 A | | 8/1997 | Kandathil et al. ............ 43/125 |
| 5,711,955 A | | 1/1998 | Karg ......................... 424/409 |
| 6,031,967 A | | 2/2000 | Flashinski et al. .......... 392/390 |
| 6,074,656 A | | 6/2000 | Katsuda et al. ............. 424/411 |
| 6,078,728 A | | 6/2000 | O'Rourke et al. .......... 392/390 |
| 6,309,986 B1 | * | 10/2001 | Flashinski et al. |

FOREIGN PATENT DOCUMENTS

| | | | |
|---|---|---|---|
| DE | 19611993 | | 4/1997 |
| DE | WO 97/35626 | * | 10/1997 ............. A61L/9/04 |
| GB | 2122903 | | 1/1984 |
| GB | 2130883 | | 6/1984 |
| GB | 2166653 | | 5/1986 |
| GB | 2 166 653 | * | 5/1986 ............. A61L/9/02 |
| WO | 99/66791 | | 12/1999 |

* cited by examiner

*Primary Examiner*—William H. Beisner
*Assistant Examiner*—Monzer R. Chorbaji

(57) ABSTRACT

Disclosed herein is two-stage mat for dispensing volatile materials. The mat is comprised of two materials varying either in thickness, thermal conductivity and/or porosity (and coated with like volatile material), or coated with volatile materials having different vaporization pressures. In either configuration, the mat provides for both an instant burst of volatile and then a sustained vaporization of volatile. Methods of using such mats are also disclosed.

11 Claims, 2 Drawing Sheets

TWO-STAGE DISPENSING MAT

CROSS REFERENCES TO RELATED APPLICATIONS

Not applicable.

STATEMENT REGARDING FEDERALLY SPONSORED RESEARCH

Not applicable.

BACKGROUND OF THE INVENTION

The present invention relates to dispensing volatile materials such as insecticides, insect repellants, fragrances, and deodorizers. It provides mats designed to be placed on an electric heater to release the volatile material when the mat is heated.

It is known in the art to impregnate or coat a solid porous cellulosic mat with a volatile material, and/or to place a volatile material in a metal pan-like mat structure. These mats are then placed on heaters to cause the volatile to vaporize into the ambient air. See generally U.S. Pat. No. 6,031,967 and WO 99/66791. The disclosure of these publications, and of all other publications referred to herein, are incorporated by reference as if fully set forth herein.

However, there can be a time lag between the initiation of the heating of the mat and when the concentration of active in the room is at a desired level. For example, when the mat contains an insecticide, it may take a few minutes before the desired level of protection from mosquitoes or other insects is achieved. This is a particular problem where the product is designed to provide a very slow, prolonged release of active (e.g. to provide overnight protection against mosquitoes).

To minimize the time lag, one could try increasing the concentration of active on the mat. However, such actives are often costly, and in any event the increased concentration may lead to unnecessarily high levels of insecticide or other active being dispensed into the air after the initial period.

Another approach to try to solve this problem would be to modify heaters so that they work at one heat during an initial phase and then work at a reduced heat at all other times. However, this would require extensive cost in revising existing heaters and, in any event, would unnecessarily increase the cost of heaters in the future.

U.S. Pat. No. 5,657,574 proposed a mosquito coil having a uniform concentration of insect control agent spread throughout it, but with the coil having an enlarged ignition end. When the coil is first lit an extra burst of insecticide is dispensed because more of the coil is burnt at that time. However, this approach is not suitable for a mat where the entire mat is to be placed on the heater at once.

WO 99/66791 provided a slab-type mat system for insertion in an indexed fashion into a heater. Discrete regions of the mat are heated in sequence. The primary purpose of the slab is to provide a mechanism for indexing a new mat section over the heater when the preceding section had been used up. However, the publication also describes that the sequential regions could carry different volatile ingredients or different concentrations of the same volatile ingredient. One example that is given is providing a high concentration section to be used at night and a low concentration section to be used during the day. Unfortunately, this requires the user to sequentially move the slab when the next stage of usage is desired.

Complicating matters is the fact that most of the inexpensive heaters used for this purpose take some time to warm up, and many do not have a fully uniform heat presentation across their face. For example, many have a hot region in the center, with progressive cooling outward. In the past, this has caused some insecticides to degrade due to exposure to the too hot central section.

Accordingly, a need still exists for an improved volatile dispensing mat.

BRIEF SUMMARY OF THE INVENTION

The present invention provides a mat for dispensing volatile vapors when heated. In one form there is a first mat substrate region having a first volatile material with an active selected from the group consisting of insect control agent, fragrance, deodorizer, and any combination thereof. There is also a second mat substrate region having a second volatile material with an active selected from the group consisting of insect control agent, fragrance, deodorizer, and any combination thereof. The first volatile material of the first mat substrate region releases at an effective rate greater than does the second volatile material of the second mat substrate region, either because of the higher and lower volatility characteristics of the first volatile material versus the second volatile material or because of selected differences between the first and second mat substrate regions. Preferably, the first region is a central region, the second region is an outward region around the central region, and the first volatile material is different from the second volatile material. A volatile material is defined as releasing at a greater or lesser "effective" rate as the intended effect of the active constituting or contained in the volatile material is achieved at a faster or slower rate.

The term "mat" is used herein to include any generally flat, thin, extended structure suitable for use with conventional mosquito mat holders, regardless of material, precise outline, texture, and other physical features such as throughholes, incorporated metallic pans, and the like. The typical commercial mosquito mat is usually a generally rectangular card made of a fibrous material, although, as just stated, the term "mat" is not confined to that particular shape or material. The term "insect control" is defined to mean killing, repelling, or otherwise altering the behavior or development of insects. "Insect control agent" is used herein in its broadest sense to include not only insecticides and repellants but also growth regulators and other agents capable of achieving insect control. "Insect" is defined to mean actual insects as well as spiders, millipedes, and other small animals commonly controlled in the same manner or with the same agents as are insects.

The first and preferably central region can be made of a metallic or other substrate which transmits heat faster than a surrounding substrate, preferably made of cellulose. This will cause different vaporization rates, even where the volatiles are the same.

One can alternatively (or in addition) retard or increase the rate of release by the selection of suitable solvents, binders, actives, and active concentrations. We prefer to use a highly volatile active for the first region, such as transfluthrin or prallethrin, esbiothrin, d-allethrin, S-bioallethrin and dichlorvos, as well as to select a metallic, thin, and nonporous substrate for the first region which will release the volatile very quickly. Particularly preferred is where the active in the volatile material of the second region is transfluthrin and the active in the volatile material of the first region is d-allethrin.

In especially preferred forms, the first and second regions are comprised of materials differing with respect to a material property selected from the group consisting of thickness, thermal conductivity, porosity, and combinations thereof. In such a case, the second region would preferably be in the form of a slab having a bore therethrough, and the first region would preferably be defined by a metal foil cup positioned in the bore. Preferably the bore and cup would be centrally located in the slab, "centrally" located being construed to mean generally centrally located or at least so located that slab material completely surrounds the bore.

Alternatively, the second region can be a ceramic slab having a recess in an upper side, and the first region can be defined by a ceramic glaze lining the recess.

In yet another variant, the second region can be a frame of cellulosic material and the first region can be a metallic tray having a recessed center extending preferably at least to the bottom surface of the frame or even further, whereupon it actually supports the frame.

In yet another form, the invention provides a mat for dispensing volatile vapors when heated. Again, there are first and second mat substrate regions, each having a volatile material with an active selected from the group consisting of insect control agent, fragrance, deodorizer, and a combination thereof. Regardless of their juxtaposition relative to each other (e.g. side by side; central and surrounding donut), the first and second regions are comprised of materials differing with respect to a material property selected from the group consisting of thickness, thermal conductivity, porosity, and combinations thereof.

In still another form, the invention provides a method for dispensing volatile vapors. One positions a mat on an electric heater. The mat has a first and a second mat substrate region having first and second volatile materials, respectively, the volatile materials each including an active selected from the group consisting of insect control agent, fragrance, deodorizer, and combinations thereof. One then simultaneously heats both the first and second mat substrate regions such that the active in the first volatile material is vaporized from the first region at a greater effective rate than the active in the second volatile material from the second region.

When used as an insect control device, the device of the invention allows the user to achieve desired protection very quickly, without sacrificing long-term protection. When dispensing a deodorizer or fragrance, the invention has the advantage of covering over existing malodors very quickly (e.g. in a bathroom), without sacrificing the ability to provide fragrance over the long term.

Importantly and surprisingly, the present invention is capable of turning a disadvantage of inexpensive heaters (non-uniform heating across the heating face) into an advantage. This is achieved by centrally placing the fast release section.

These and still other advantages of the invention will appear from the following description. In the description reference is made to the accompanying drawings in which there is shown by way of illustration preferred embodiments of the invention. However, the claims should be looked to in order to judge the full scope of the invention.

DETAILED DESCRIPTION OF THE PREFERRED EMBODIMENTS

Figure 1:
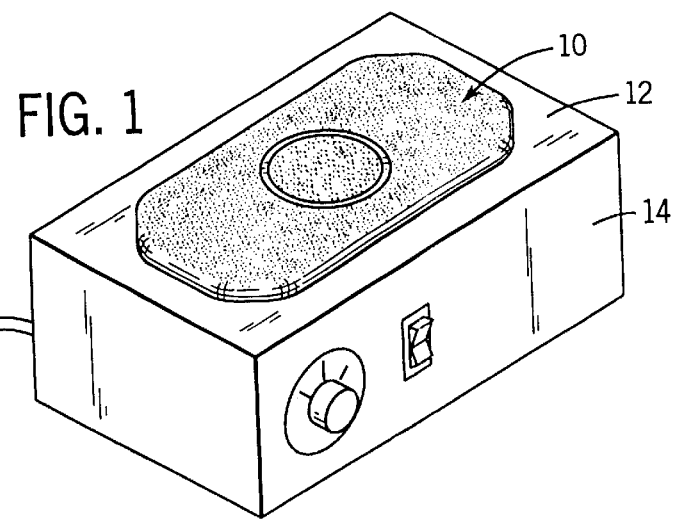
FIG. 1 is a perspective view of a two-stage mat of the present invention being used with an electric heater.

Referring first to FIG. 1, two-stage mat 10 is shown placed upon a horizontal burner face 12 of an electric heater 14. The term "burner face" refers to the heated surface (typically solid but alternatively a mesh or other structure) of an electric heater on which it is intended that a user place a mosquito mat for heating. The heater 14 can be an electrical-resistance heater such as the heater sold by in Italy and other countries as the RAID® heater by S.C. Johnson & Son, Inc. However, other heaters could also be used without limitation on the horizontal, vertical, or other orientation of their heating surfaces.

Figure 2A:
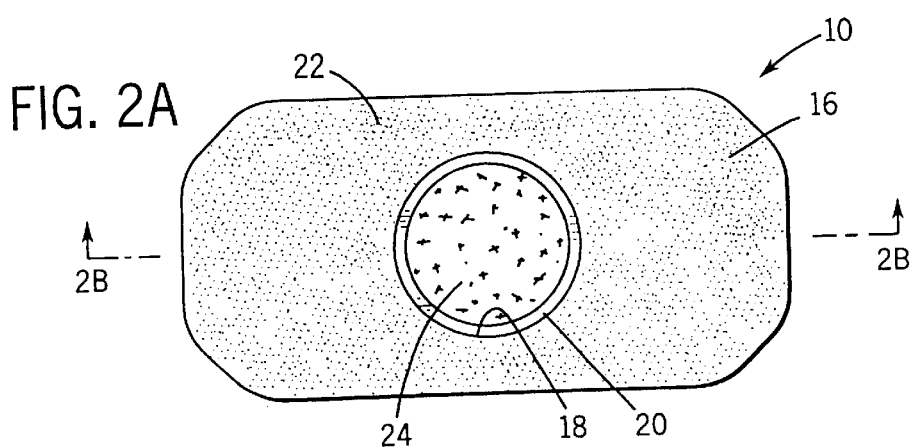
FIG. 2A is a top view of a first embodiment of the two-stage mat of the present invention.
Figure 2B:
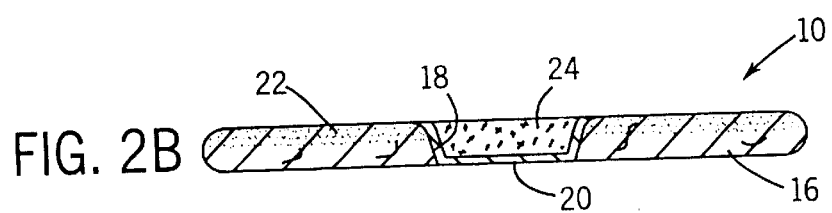
FIG. 2B is a cross-sectional view taken along line 2—2 of FIG. 2A.

A first preferred embodiment of the mat is shown in FIGS. 2A and 2B. Although other embodiments of the mat are shown, all generally include two non-integral substrate sections. Each is impregnated or coated with the same or different volatile materials. The substrates preferably have distinctly different volatile release parameters, such as thickness, thermal conductivity, and/or porosity. The volatile materials or formulations may also have distinctly different vaporization rates.

The first embodiment of the mat 10 includes a slab-like body 16 having a generally cylindrical bore 18 therethrough. The bore 18 is lined with a cup-shaped insert 20 that is preferably adhered to the body 16 by an adhesive at the inner diameter of the bore 18.

The body 16 and the insert 20, respectively, are impregnated and coated with volatile materials or formulations. When placed over the heater 12, the volatile is released from the mat 10 (when the mat 10 is heated). Advantageously, the bore 18 is essentially in the center of the body 16, which takes advantage of the often higher temperatures in the center of the burner surface typically associated with low cost heaters.

The body 16 is preferably a pulp or other cellulose-based material formed into a slab of approximately 3.5 cm×1.75 cm.×0.25 cm. The insert 20 is preferably a metallic foil approximately 0.5 mm thick, such as an aluminum alloy foil. The insert 20 is adhered to the inner diameter of the bore 18 by a polymeric adhesive, such as adhesive "711" (commercially available from Manufacturer Resources, Inc. of New Berlin, Wis.).

Preferably, body 16 is impregnated with a second volatile material 22 having a slower releasing active ingredient and the inside surface of the insert 20 is coated with a chemically distinct first volatile material 24 having a faster releasing active ingredient. As an insect control device, preferably second volatile material 22 is 100 mg of a liquid solution having a chemical composition of 40% d-allethrin (an insecticide active ingredient), 40% piperonyl butoxide (PBO, synergist/release agent), and 20% Isopar M (solvent). First volatile material 24 is preferably 50 mg of a liquid solution having a chemical composition of 4% transfluthrin (insecticide active ingredient) and 96% Isopar E (solvent). Transfluthrin vaporizes more quickly than does the d-allethrin because it has a higher vaporization pressure.

Note also that insert 20 has a significantly decreased thickness and porosity (and increased thermal conductivity) relative to the body 16. Moreover, the insert 20 is coated with a faster releasing volatile material 24 than that with which the body 16 is impregnated. In this preferred construction using the above selected materials, when the mat 10 is heated, the mat 10 provides for an instant burst of the first volatile material 24 at startup of the heater 16. It also provides uniform and efficient sustained release of second volatile material 22 for prolonged protection lasting at least 6 to 8 hours and as much as a day or more.

It should be noted that other materials could be selected that would provide two-stage vaporization. For example, the body 16 could be made of other solid porous substrates, such as sintered glass, a polymeric block, plastic beads, natural or synthetic fabrics, and other absorbent and adsorbent materials. The insert 20 could be any other suitable metallic foil (or even other substrates), and the adhesive used to join the insert 20 to the body 16 can be any other acrylic, urethane, or other adhesive resistant to high temperatures.

Alternatively, the volatile materials 22 and 24 could be any other suitable known insecticides, repellants, growth regulators, or other insect control agent. For example, the volatile materials 22 and 24 could include organic phosphorus insecticides, lipidamide insecticides, natural repellants such as citronella oil, natural pyrethrum and pyrethrum extract, and synthetic pyrethroids. Suitable synthetic pyrethroids include allethrin as d-allethrin, allethrin, benfluthrin, bifenthrin, S-bioallethrin, esbiothrin, esbiol, bioresmethrin, cycloprothrin, cyfluthrin, beta-cyfluthrin, cyhalothrin, deltamethrin, empenthrin, esfenvalerate, fenpropathrin, fenvalerate, flucythrinate, tau-fluvalinate, kadethrin, permethrin, phenothrin, prallethrin, resmethrin, tefluthrin, tetramethrin or tralomethrin. Other volatile insecticides as described in U.S. Pat. No. 4,439,415 can also be used.

Volatile insect growth control agents such as methoprene and hydroprone may also be used. Alternatively or in addition, fragrances and deodorizers may be used, such as imonene, eucalyptus, and citronella.

We tested the FIG. 2A mat as follows. Groupings of four test mats (with specified ages) were prepared, one being a standard single-stage pulp body mat and the other three being the FIG. 2A two-stage mat of the present invention and constructed as described above. One of the three had active only in the center, one had active only in the peripheral substrate, and one had active in both.

The test conditions and volatile materials used for each mat are as follows.

| Mat# | Mat Type | Volatile Composition |
| --- | --- | --- |
| 1 | standard | PF-40%; PBO-40%; IM-20% |
| 2 | outside only | PF-40%; PBO-40%; IM-20% |
| 3 | center only | T-4%; IE-96% |

-continued

| Mat# | Mat Type | Volatile Composition |
| --- | --- | --- |
| 4 | 2-stage | body: PF-40%; PBO-40%; IM-20% insert: T-4%; IE-96% |

PF = d-allethrin (insecticide)
PBO = piperonyl butoxide (insecticidal synergist)
IM = Isopar M (solvent)
T = transfluthrin (insecticide)
IE = Isopar E (solvent)

The study was conducted in a 0.42 cubic meter glass chamber using ten free-flying female *culex quinquefasciatus* (mosquitoes). The mats, heaters and mosquitoes were all introduced into the chamber at the same time.

Mean knockdown percentage data was collected for each thirty second time interval. Knockdown data was also collected in thirty second intervals until 100% knockdown was achieved, or until the expiration of twenty minutes.

The study showed that knockdown began much earlier using the two-stage mat (MAT3) of the present invention than the standard single-stage mat (MAT1). The same was true for the time necessary to achieve 100% knockdown.

FIGS. 3–7 illustrate alternate embodiments of the present invention, wherein similar components are referred to with similar reference numbers, albeit with an A, B, C, D or E suffix. Unless indicated otherwise, the alternate embodiments preferably use the same materials and volatile materials mentioned above with respect to the first embodiment. Moreover, the alternate embodiments are used in the same manner as the first embodiment, providing for multiple rate vaporization of the volatile materials when sufficiently heated by a heater.

Figure 3:
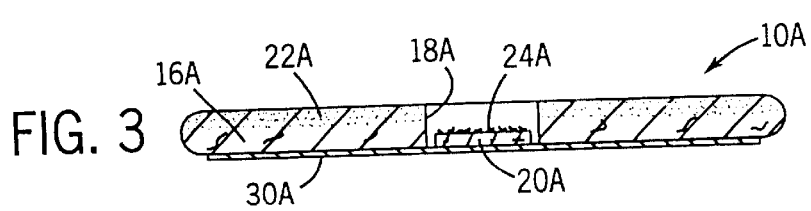
FIG. 3 is a vertical cross-sectional view of a second embodiment of the present invention.

Referring now to FIG. 3, mat 10A includes a cellulosic body 16A having a through bore 18A at its center. A metallic foil layer 30A is adhered to the bottom side of the entire body 16A to distribute heat more evenly along the bottom side of the body 16A. A thin pulp insert 20A, preferable made of a filter paper, is adhered to a top side of the foil layer 30A within the through bore 18A so that it does not contact the pulp body 16A directly. The pulp body 16A is impregnated with a slow release volatile material 22A and the insert 20A is impregnated with a fast release volatile 24A. The separation minimizes leaching of the respective volatiles into each other's region during storage.

Figure 4:
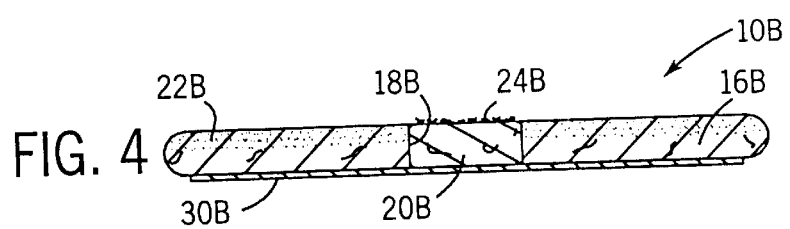
FIG. 4 is a vertical cross-sectional view of a third embodiment of the present invention.

In the embodiment shown in FIG. 4, the mat 10B includes a pulp body 16B having a central through bore 18B in which is disposed a plug insert 20B of the same material and thickness. Preferably, the plug insert 20B is the material removed from the body 16B when the through bore 18B is created. This mat 10B also includes a metallic foil layer 30B adhered to the bottom side of the body 16B and the plug insert 20B. Like before, the body 16B is impregnated with a slow release volatile material 22B and the plug insert 20B is impregnated with a fast release volatile material 22B. In this embodiment, the plug insert 20B should be treated with the volatile material 24B and allowed to dry prior to assembly so that the volatile material 24B does not bleed into the body 16. Similarly, the volatile material 22B should be impregnated into the body 16B and allowed to dry before the plug is inserted.

Figure 5A:
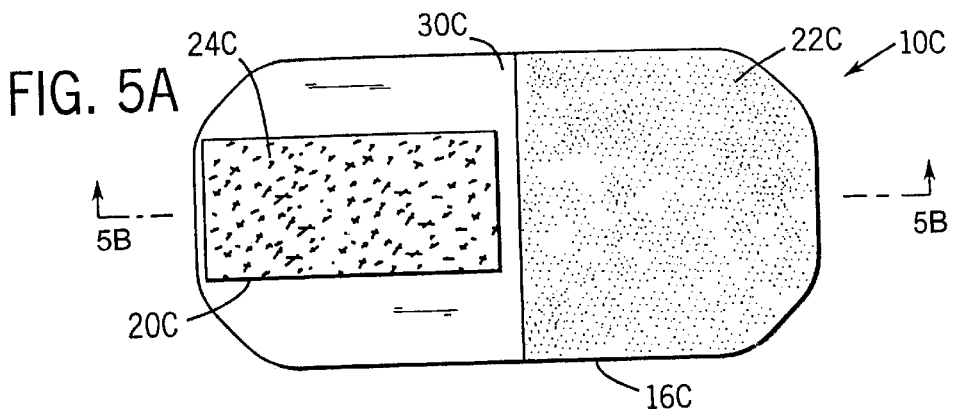
FIG. 5A is a top view of a fourth embodiment of the present invention.
Figure 5B:
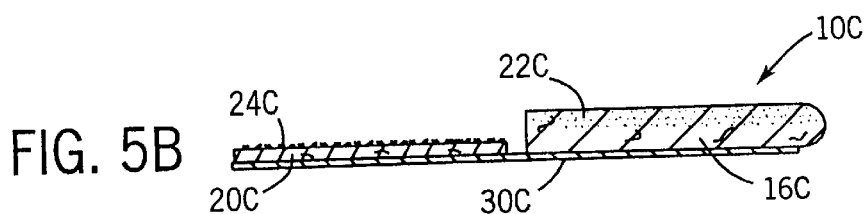
FIG. 5B is a cross-sectional view taken along line 5—5 of FIG. 5A.

Referring now to FIGS. 5A and 5B, the mat 10C includes a pulp body 16C roughly half the length of the prior embodiments. The body 16C is adhered at its bottom side to a full-length metallic foil layer 30C to which is also adhered a thin pulp material strip 20C, preferably made of filter paper less porous than the pulp of the body 16C. The strip 20C is adhered to the foil layer 30C so as not to contact the body 16C. The body 16C is impregnated with a slow release volatile material 22C and the strip 20C is impregnated with a fast release volatile material 24C. As in mat 10A (see FIG. 3), the decreased thickness and less porosity of the strip 20C further aids in rapid vaporization of the fast release volatile material 24C.

Figure 6:
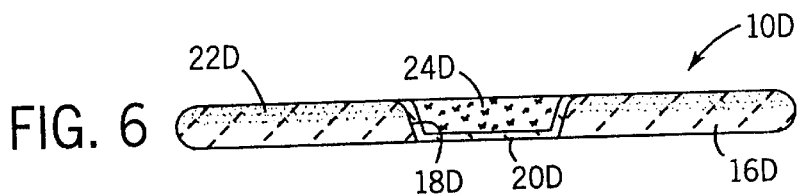
FIG. 6 is a vertical cross-section view of a fifth embodiment of the present invention.

Referring now to FIG. 6, the mat 10D includes a slab-like body 16D made of a ceramic material such as terra cotta or earthenware. The body 16D includes a central, dished recess 18D that is lined by a suitable ceramic glaze, such as silica-based low fire clear glaze. The ceramic glaze liner 20D is preferably less porous than the ceramic of the body 16D. This feature, and the decreased thickness under the glaze, allows more rapid vaporization of a fast release volatile material 24D coating the liner 20D. As before, the body 16D is impregnated with a slow release volatile material 22D.

Figure 7A:
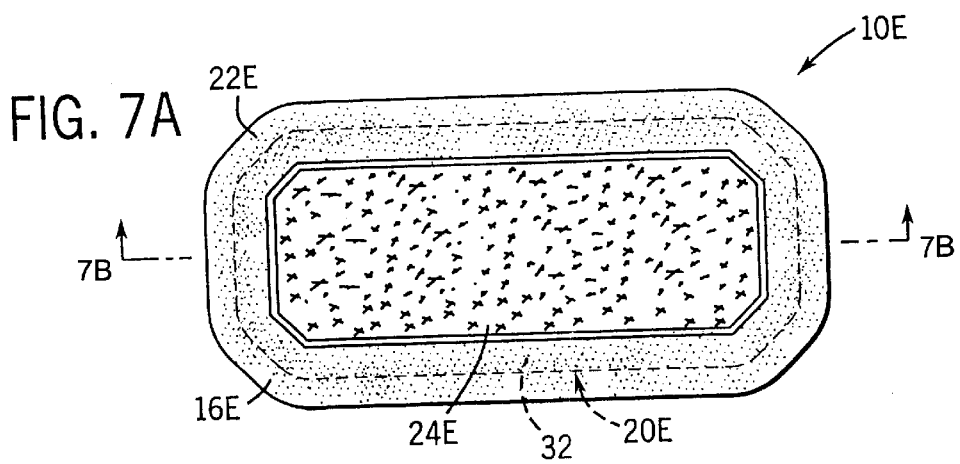
FIG. 7A is a top view of a sixth embodiment of the present invention.
Figure 7B:
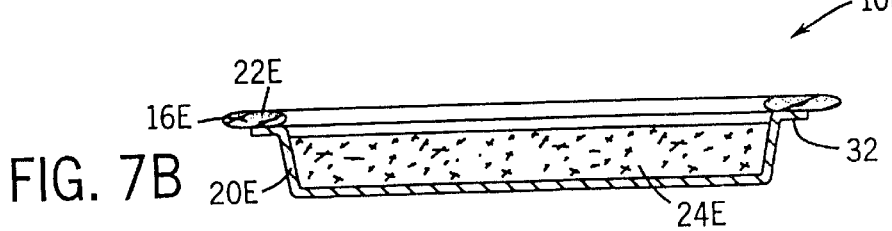
FIG. 7B is a vertical cross-sectional view taken along line 7—7 of FIG. 7A.

Referring now to FIGS. 7A and 7B, rather than having a slab-like body, mat 10E has a pulp frame 16E which rests upon a raised perimeter rim 32 of a metallic foil tray 20E having a recessed center. The frame 16E is impregnated with a slow release volatile material 22E and the tray 20E is coated with a fast release volatile material 24E.

It should be appreciated that the mats of the present invention could be formed in still other embodiments. These are also intended to be within the scope of the present invention. For example, a single volatile material could be used and still provide for two-stage vaporization, provided that there are two or more substrates having different volatile release properties, such as thickness, thermal conductivity and porosity.

Moreover, the two-stage mat of the present invention could also be a disinfectant/fragrancer/deodorizer, using any of a wide variety of active ingredients for such purposes, including glycols, trimethylene and dipropylene known in the art. Further, even with the same active and substrates, a FIG. 4 like structure could work if solvents, binders, and the like were adjusted to suitably control release rates. Accordingly, the claims should be referenced in order to determine the full scope of the invention.

INDUSTRIAL APPLICABILITY

The invention provides mats for the controlled release of insect control agents, fragrances, disinfectants, and similar useful, volatile materials, where a burst of a volatile material occurs when the product is first used, followed by a prolonged release of the same or another volatile.

What is claimed is:

1. A mat for dispensing volatile vapors when heated, comprising:
   a first mat substrate region having a first volatile material with an active selected from the group consisting of insect control agents, fragrances, deodorizers, and combinations thereof; and
   a second mat substrate region, not part of the first mat substrate region, having a second volatile material different from the first volatile material with an active selected from the group consisting of insect control agents, fragrances, deodorizers, and combinations thereof;
   wherein the first mat substrate region is a central region and the second mat substrate region is an outward region around the central region, and the first volatile material of the first mat substrate region releases at a rate greater than does the second volatile material of the second mat substrate region in response to heating of the mat.

2. The mat of claim 1 wherein the first volatile material of the first mat substrate region is more volatile than is the second volatile material of the second substrate region.

3. The mat of claim 1 wherein physical or chemical characteristics of the first and second mat substrate regions are selected to be such that the first volatile material of the first mat substrate region is volatilized faster than is the second volatile material of the second substrate region.

4. The mat of claim 1, wherein when the mat is positioned on a heater so as to simultaneously heat both the first and second mat substrate regions the active in the first volatile material can be vaporized from the first mat substrate region at a greater rate than is the active in the second volatile material.

5. The mat of claim 1, wherein the first and second regions are comprised of materials differing with respect to a material property selected from the group consisting of thickness, thermal conductivity, porosity and combinations thereof.

6. The mat of claim 5, wherein the first region is formed from a cellulosic material and the second region is formed from a metallic material.

7. The mat of claim 6, wherein the second region is in the form of a slab having a bore therethrough and the first region is defined by a metal foil cup positioned in the bore.

8. The mat of claim 1, wherein the second region is a ceramic slab having a recess in an upper side, and the first region is defined by a ceramic glaze lining the recess.

9. The mat of claim 1, wherein the second region is a frame of cellulosic material and the first region is a metallic tray having a recessed center.

10. The mat of claim 1, wherein the first volatile material has a different vaporization rate from the mat than the second volatile material.

11. The mat of claim 1, wherein the active in the first volatile material is transfluthrin and the active in the second volatile material is d-allethrin.

* * * * *